US007205162B1

(12) United States Patent
Mosbach et al.

(10) Patent No.: US 7,205,162 B1
(45) Date of Patent: *Apr. 17, 2007

(54) ARTIFICIAL ANTIBODIES, METHOD OF PRODUCING THE SAME AND USE THEREOF

(75) Inventors: Klaus Mosbach, Lackalänga 31, S-244 94, Furulund (SE); Georg Vlatakis, Crete (GR); Lars I. Andersson, Eslöv (SE); Ralf Müller, Henstedt-Ulzburg (DE)

(73) Assignee: Klaus Mosbach, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/305,738

(22) Filed: May 6, 1999

Related U.S. Application Data

(63) Continuation of application No. 08/433,514, filed on Dec. 7, 1995, now abandoned.

(51) Int. Cl.
*G01N 33/549* (2006.01)
*G01N 33/533* (2006.01)
*G01N 33/553* (2006.01)
*A61K 39/44* (2006.01)

(52) U.S. Cl. .................. 436/535; 436/531; 436/532; 436/533; 436/534; 436/544; 436/545; 436/501; 436/546; 436/815; 436/816; 424/130.1; 424/164.1; 424/175.1

(58) Field of Classification Search ................ 436/531, 436/532, 533, 534, 535, 816, 815, 544, 501, 436/546, 545; 424/130.1, 175.1, 164.1
See application file for complete search history.

(56) References Cited

U.S. PATENT DOCUMENTS

| 4,269,605 A | | 5/1981 | Dean et al. | |
| 5,110,833 A | * | 5/1992 | Mosbach .................. | 530/388.9 |
| 5,310,648 A | | 5/1994 | Arnold et al. | |
| 5,372,719 A | | 12/1994 | Afeyan et al. | |
| 5,453,199 A | | 9/1995 | Afeyan et al. | |
| 5,630,978 A | * | 5/1997 | Domb ...................... | 526/238.1 |
| 5,756,717 A | * | 5/1998 | Paliwal et al. ............ | 536/123.1 |
| 5,872,198 A | * | 2/1999 | Mosbach et al. ........... | 526/221 |
| 5,994,110 A | * | 11/1999 | Mosbach et al. ........ | 435/173.1 |

FOREIGN PATENT DOCUMENTS

| DE | 2 358 647 | 11/1973 |
| EP | 0 364 772 | 9/1989 |
| EP | 0 552 630 | 1/1993 |
| GB | 1133328 | 2/1966 |
| JP | 60 181155 | 9/1985 |
| SE | 8404967 | 4/1986 |
| WO | WO 90/07527 | 7/1990 |
| WO | WO 92/19663 | 11/1992 |
| WO | WO 94/11403 | 5/1994 |
| WO | WO 94/14835 | 7/1994 |

OTHER PUBLICATIONS

D. O'Shannessy et al, J. of Chromatography (1989), vol. 470, pp. 391-399.*
D. O'Shannessy et al, Analytical Biochemistry (1989), vol. 177, pp. 144-149.*
Andersson et al., "Imprinting of Amino Acid Derivatives in Macroporous Polymers," Tetrahedron Letters, 1984, pp. 5211-5214, 25(45).
Andersson and Mosbach, "Enantiomeric resolution on molecularly imprinted polymers prepared with only non covalent and non-ionic interactions," J. Chromatography, 1990, pp. 313-322, vol. 516, Elsevier Science Publishers B.V.
Andersson et al., "Enantiomeric resolution of amino acid derivatives on molecularly imprinted polymers as monitored by potentiomeric measurements," J. Chromatography, 1990, pp. 323-331, vol. 516, Elsevier Science Publishers B.V.
Andersson et al., "Bioseparation and Catalysis in Molecularly Imprinted Polymers"; Molecular Interactions in Bioseparations, (That. T. Ngo, ed.), 1993, pp. 383-394, Plenum Press.
Andersson et al., "Molecular recognition in synthetic polymers: preparation of chiral stationary phases by molecular imprinting of amino acid amines," J. Chromatography, 1990, pp. 167-179, vol. 513, Elsevier Science Publishers B.V.
Arshady et al., "Synthesis of Substrate-Selective Polymers by Host-Guest Polymerization," Makromol. Chem., 1981, pp. 687-692, 182.
Braun and Kuchen., "Ionenselective Austauscherharze durch vernetzende Copolymerisation vinylsubtituierter Metallkomplexe," Chemiker-Zeitung, Jul./Aug. 1984, pp. 255-257, 108.
Bystrom et al., "Selective Reduction of Steroid 3- and 17-Ketones Using LiAlH$_4$ Activated Template Polymers," Journal Am. Chem. Soc., 1993, pp. 2081-2083, vol. 115.
Chang et al., "Protein Separation and Purification in Neat Dimethyl Sulfoxide," Biochemical and Biophysical Research Communications, 1991, pp. 1462-1468, 176(3).
Damen et al., "Stereoselective Synthesis Via a Photochemical Template Effect," Journal Am. Chem. Soc., Apr. 23, 1980, pp. 3265-3267, 102(9), American Chemical Society, Washington, DC.
Ekberg and Mosbach, "Molecular imprinting: a technique for producing specific separation materials," TIBTECH, Apr. 1989, pp. 92-95, vol. 7, Elsevier Science Publishers Ltd (UK).

(Continued)

*Primary Examiner*—Mary E. Ceperley
(74) *Attorney, Agent, or Firm*—Morgan & Finnegan, L.L.P.

(57) ABSTRACT

Artificial antibodies or antibody mimics are described. They consist of polymers that carry specific binding sites mimicking the properties of antibodies. There is also described a method for producing artificial antibodies, in which polymerisable monomers carrying functional groups and crosslinking monomers are polymerised in the presence of a print molecule and subsequently the print molecule is removed leaving specific binding sites complementary to the print molecules.

There are also described methods for determination and isolation of organic molecules using the artificial antibodies as well as therapeutic and diagnostic methods using these antibodies.

41 Claims, 2 Drawing Sheets

OTHER PUBLICATIONS

Figuera et al., "High-Performance Immobilized-Metal Affinity Chromatography of Proteins on Iminodiacetic Acid Silica-Based Bonded Phases," Journal of Chromatography, 1986, pp. 335-377, 371, Elsevier Science Publishers B.V. Amsterdam.

Fischer et al., "Direct Enantioseparation of β-Adrenergic Blockers Using a Chiral Stationary Phase Prepared by Molecular Imprinting," J. Am. Chem. Soc., 1991, pp. 9358-9360, vol. 113, American Chemical Society, Washington, DC.

Glad et al., "Use of Silane Monomers for Molecular Imprinting and Enzyme Entrapment in Polysiloxane-Coated Porous Silica," J. Chromatography, 1985, pp. 11-23, vol. 347, Elsevier Science Publishers B.V.

Guyot, A., "Synthesis and Structure of Polymer Supports," Syntheses and Separations using Functional Polymers, 1988, pp. 1-43, John Wiley & Sons Ltd, Chichester, United Kingdom.

Hedborg et al., "Some studies of molecularly-imprinted polymer membranes in combination with field-effect devices," Sensors and Actuators A-physical, 1993, pp. 796-799, vol. A37-A38; proceedings of Eurosensors VI, San Sebastian, Spain, Oct. 5-7, 1992, Elsevier Sequoia, Lausanne, Switzerland.

Johansson and Mosbach, "Acrylic Copolymers as Matrices for the Immobolization of Enzymes," Biochemica et Biophysica Acta, 1974, pp. 339-347, vol. 370, Elsevier Scientific Publishing Company, Amsterdam, The Netherlands.

Kempe and Mosbach, "Chiral recognition of $N^\alpha$-protected amino acids and derivatives in non-covalently molecularly imprinted polymers," Int. J. Pept. Protein Res., Dec. 1994, pp. 604-606, 44(6), Munksgaard International Publishers, Belgium.

Kempe and Mosbach, "Direct resolution of naproxen on a non-covalently molecularly imprinted chiral stationary phase," J. Chromatrography, 1994, pp. 276-279, 664, Elsevier Science B.V.

Kempe and Mosbach, "Binding Studies on Substrate and Enantio-Selective Molecularly Imprinted Polymers," Analytical Letters, 1991, pp. 1137-1145, 24(7), Marcel Dekker, Inc.

Mayes et al., "Sugar Binding Polymers Showing High Anomeric and Epimeric Discrimination Obtained by Noncovalent Molecular Imprinting," Analytical Biochemistry, Nov. 1, 1994, pp. 483-488, 222(2), Academic Press, Inc.

Morawetz and Song, "The Interaction of Chain Molecules Carrying Reactive and Catalytic Chain Substituents," Journal Am. Chem. Soc., Dec. 20, 1966, pp. 5714-5718, 88(24).

Mosbach, "Enzymes Bound to Artificial Matrixes," Scientific American, Mar. 1971, pp. 26-33.

Mosbach and Klaus, "Molecular imprinting," Trends in Biochemical Sciences, Jan. 1994, pp. 9-14, vol. 19, Elsevier Science Publishers.

Morris et al., "Synthesis of Some Amino Acid Derivatives of Styrene," JACS, 1959, pp. 377-382, vol. 81.

Munzer and Trommsdorff, "Polymerizations In Suspension" Polymerization Processes, 1977, pp. 106-143, John Wiley & Sons, New York, United States of America.

Nilsson, "Enzymatic synthesis of oligosaccharides," Trends in Biotechnology, Sep. 1988, pp. 256-264, 6(9), Elsevier Publications, Cambridge, United Kingdom.

Nilsson et al., "The use of bead polymerization of acrylic monomers for immobilization of enzymes," Biochima et Biophysica Acta, 1972, pp. 253-256, vol. 268.

Norrlow et al., "Improved Chromatography: Prearranged Distances Between Boronate Groups by the Molecular Imprinting Approach," J. Chromatography, 1987, pp. 374-377, vol. 396, Elsevier Science Publishers B.V. Amsterdam.

Norrlow et al., "Acrylic Polymer Preparations Containing Recognition Sites Obtained by Imprinting with Substrates," J. Chromatography, 1984, pp. 29-41, 229(1), Elsevier Science Publishers B.V., Amsterdam, The Netherlands.

O'Shannessy et al., "Molecular Recognition in Synthetic Polymers," Journal Molecular Recognition, Jul. 1989, pp. 1-5, 2(1), Heydon & Sons Limited.

Paine, "Dispersion Polymerization of Styrene in Polar Solvents. IV Solvency Control of Particle Size from Hydroxypropyl Cellulose Stabilized Polymerizations," Journal of Polymer Science, Aug. 1990, pp. 2485-2500, vol. 28, John Wiley & Sons, Inc.

Pelzbauer et al., "Reactive Polmers," Journal of Chromatography, 1979, pp. 101-107, vol. 171, Elsevier Science Publishing Company, Amsterdam, The Netherlands.

Porath et al., "Metal Chelate Affinity Chromatography, A New Approach to Protein Fractionation," Nature, Dec. 18, 1975, pp. 598-599, vol. 258.

Ramstrom et al., "Recognition Sites Incorporating Both Pyridinyl and Carboxy Functionalities Prepared by Molecular Imprinting," J. Org. Chem., 1993, pp. 7562-7564, vol. 58.

Ramstrom et al., "Synthetic Peptide Receptor Mimics: Highly Stereoselective Recognition in Non-Covalent Molecularly Imprinted Polymers," Tetrahedron: Assymetry, 1994, pp. 649-656, 5(4), Elsevier Science Ltd.

Reinholdsson et al., "Preparation and properties of porus particles from trimethylolpropane trimethacrylate," Die Angewandte Makromolekulare Chemie, 1991, pp. 113-132, vol. 192, Huthig & Wepf Verlag, Basel, Switzerland.

Schmid et al., "Porosity determination of poly(trimethylolpropane trimethacrylate) gels," Makromol. Chem., May 1991, pp. 1223-1235, vol. 192, Huthig & Wepf Verlag, Basel, Switzerland.

Sellergren, "Imprinted dispersion polymers: a new class of easily accessible affinity stationary phases," J. Chromatography, 1994, 113-141, vol. 673, Elsevier Science B.V.

Sellergren, "Direct Drug Determination by Selective Sample Enrichment on an Imprinted Polymer," Anal. Chem., May 1, 1994, pp. 1578-1582, 66(9).

Stahl et al., "The Synthesis of a D-Amino Acid Ester in an Organic Media with a α-Chymotrypsin Modified by a Bio-Imprinting Procedure," Biotechnology Letters, 1990, pp. 161-166, 12(3).

Vlatakis et al., "Drug assay using antibody mimics made by molecular imprinting," Nature, Feb. 18, 1993, pp. 645-647, vol. 361.

Tamao, et al. "Stereochemistry at Carbon in Cleavage of the Carbon-Silicon Bond in exo- and endo-2-Norbornylpentaflourosilicates by Various Brominating Agents," Journal Am. Chem. Soc., Apr. 23, 1980, pp. 3267-3269, 102(9), American Chemical Society, Washington, DC.

Williamson et al., "The Preparation of Micron-Size Polymer Particles in Nonpolar Media," Journal of Colloid and Interface Science, Oct. 1987, pp. 559-564, 119(2), Academic Press, Inc.

Weith et al., "Synthesis of Cellulose Derivatives Containing the Dihydroxyboryl Group and a Study of Their Capacity to Form Specific Complexes with Sugars and Nucleic Acid Components," Biochemistry, 1970, pp. 4396-4401, 9(22).

Wulff et al., "Enzyme-Analog Built Polymers. 26. Enantioselective Synthesis of Amino Acids Using Polymers Possessing Chiral Cavities Obtained by Imprinting Procedure with Template Molecules," Chemical Abstracts, Jan. 29, 1990, 112(5), American Chemical Society, Columbus, Ohio, United States of America, pp. 640.

Wulff et al., "Enantioselective Synthesis of Amino Acids Using Polymers Possessing Chiral Cavities Obtained by an Imprinting Procedure with Template Molecules," Enzyme-Analogue Built Polymers, 26 Makromol. Chem., 1989, pp. 1727-1735, 190(7).

Wulff et al., "Enzyme-Analogue Built Polymers, 18 Chiral Cavities in Polymer Layers Coated in Wide-Pore Silica," Reactive Polymers, 1985, pp. 261-275, vol. 3.

Wulff et al., "Influence of the nature of the crosslinking agent on the performance of imprinted polymers in racemic resolution," Makromol. Chem., 1987, pp. 731-740, vol. 188.

Wulff, "Polymeric Reagents and Catalysts," ACS Symposium Series, Developed from a symposium sponsored by the Divisions of Organic and Polymer Chemistry at the American Chemical Society, Miami Beach, Florida, Apr. 28-May 3, 1985, pp. 186-230.

Wulff et al., "Racemic Resolution of Free Sugars with Macroporus Polymers Prepared by Molecular Imprinting. Selectivity Dependence on The Arrangement of Functional Groups Versus Spatial Requirements," J. Org. Chem., Jan. 4, 1991, pp. 395-400, 56(1), American Chemical Society.

Wulff et al., "The role of binding site interactions in the molecular imprinting of polymers," Trends in Biotechnology, Mar. 1993, pp. 85-87, vol. 11, Elsevier Science Publishers Ltd (UK).

* cited by examiner

ARTIFICIAL ANTIBODIES, METHOD OF PRODUCING THE SAME AND USE THEREOF

This is a continuation of application Ser. No. 08/433,514; Filed Dec. 7, 1995 now abandoned.

The present invention concerns artificial antibodies, a method for producing the artificial antibodies, a method for determination of an organic molecule in a fluid sample, a method for separation or isolation of an organic molecule and use of the latter methods in immunoassays as well as a method of therapy or diagnostics.

Antibodies are used in several areas, such as therapy, immunoaffinity, purification and in particular in immunoassays. As to the latter aspect the corresponding antigens can either be small or large molecules.

Antibodies are normally produced by immunising animals with the corresponding antigen leading to polyclonal antibodies, or by using fused cells (B cells) allowing the obtained cell lines to produce monoclonal antibodies.

Recent efforts in obtaining other biologically derived antibodies or at least antibody-like compounds involve recombinant techniques applied to bacteria or plants.

Antibodies can be raised against most compounds; they are versatile reagents employed in numerous applications[1-5], ranging from basic research to clinical analysis. However, being bio-macromolecules they require careful handling and their production is costly[5].

A potentially useful alternative would be the production of non-biologically derived antibody mimics or artificial antibodies, such as polymer structures that are similar to biological antibodies in binding and recognising antigens.

The inherent advantages of such systems would be that the need for animal sources is obliviated, and that antibody mimics can be obtained for cases where it is difficult or impossible to raise antibodies, as for immuno suppressive agents, such as cyclosporin, certain structures, such as macrolides or short peptides.

Furthermore, such non-biological systems could be made more stable, allowing repeated use, higher temperatures and easy sterilisation.

In addition the need for derivatisation of antigens for immunisation purposes is made unnecessary, thereby avoiding the often complicated chemistry and sometimes decreased recognition for the original target molecule (=antigen).

Since the development of the first radioimmunoassay[1], immunological techniques using labelled reactants have gained an extraordinary prominence in the field of medical research and in clinical diagnosis. In particular, the discovery of monoclonal antibodies[2] and their use in immunoassays has offered novel advantages and more possibilities. Despite the plethora of markers and different procedures[3,4] that have been employed, all the immunological techniques exploit the remarkable affinity and specificity of antibodies. However, antibodies are labile bio-molecules which require careful handling and storage. Their production is a time-consuming procedure[5], including several laborious steps like conjugation of the hapten to a carrier protein, immunisation of animals and isolation of immunoglobulins.

Thus, there was a need for an immunoassay-like technique in which stable and easily prepared highly selective polymers, rather than antibodies are used.

The technique of molecular imprinting has attracted much attention in the last few years[6-8]. Recently, molecular imprinting has been developed to a stage of practical application in enantiomeric separations[11-15], in particular in the resolution of racemic drugs such as β-blockers[16].

Furthermore, the technique has been applied to make synthetic enzymes[9,10].

The technique of molecular imprinting and its special form of non-covalent imprinting as developed by the inventors makes it possible to achieve the above objects.

Briefly, the technique involves polymerisation of functional monomers in the presence of a print molecule (see FIG. 2). Subsequent removal of the print molecule from the rigid polymer results in sites within the polymer that are complementary to and have an affinity for the original print molecule.

According to the invention there are provided artificial antibodies, which consist of polymers that carry specific binding sites mimicking the properties of antibodies.

There is also provided, according to another aspect of the invention, a method for producing artificial antibodies, in which polymerisable monomers carrying functional groups and crosslinking monomers are polymerised in the presence of a print molecule and subsequently the print molecule is removed leaving specific binding sites complementary to the print molecule.

The invention also provides for a method for determination of an organic molecule in a fluid sample. According to this method, a known amount of the organic molecule provided with a label is added to the sample, the sample is contacted with artificial antibodies having specific binding sites for the organic molecule, whereby the labelled and unlabelled organic molecules are competitively bound to the binding sites, and the labelled organic molecule is determined either unbound in the supernatant or bound by the polymer.

There is also provided a method for separation or isolation of an organic molecule from a fluid sample, in which the sample, labelled or not, is contacted with an excess of artificial antibodies consisting of a polymer having specific sites for the organic molecule, whereby the organic molecule is bound to the binding sites, and optionally the organic molecule is measured bound to the artificial antibodies or eluted from the antibodies.

The invention also provides for a method of therapy or diagnosis, in which artificial antibodies are administrated to a mammal body, which artificial antibodies consist of a biocompatible polymer carrying specific binding sites mimicking the properties of antibodies towards an organic molecule.

Figure 1:
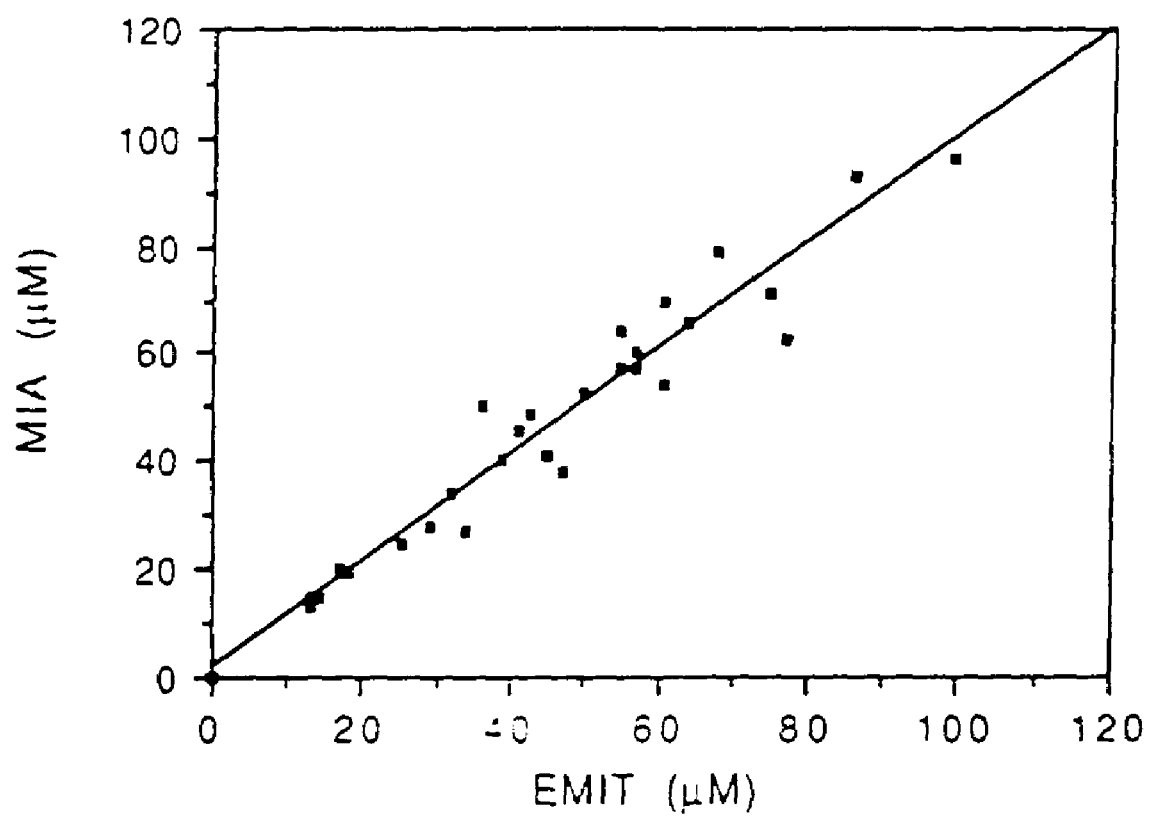
FIG. 1. Example benzodiazepine structures.

In one embodiment of the invention, the polymers are prepared by non-covalent polymerisation.

The polymers constituting the artificial antibodies are preferably built up of polymerisable monomers carrying functional groups and crosslinking monomers. Preferably the polymerisable monomers carrying functional groups are chosen among negatively charged monomers such as methacrylic acid, itaconic acid, basic monomers such as vinylpyridine, vinylimidazole, hydrophobic monomers carrying alkyl chains, monomers allowing π-π-interactions, van der Waals forces.

In one embodiment of the invention, polymers are built up of methacrylic acid crosslinked by ethylene glycol dimethacrylate.

If the artificial antibodies are to be used for administration to a mammal body the polymers must be bio-compatible. Preferably they must be of the size not more than 5 µm or the size of normal biological antibodies, most preferred 10–100 nm.

In preparation of artificial antibodies according to the invention, the polymer is ground to a particle size of normally ~25 µm for use in so-called heterogenous assays.

The fines, that is particles with a size of 10–100 or 1000 nm, resulting from the grinding, can be kept in solution or suspension and used for instance in so-called homogenous immunoassays. Such assays are extremely sensitive and can be performed involving e.g. two different antibodies.

Another advantage with the fine particles is that they are more suitable for use in therapy or diagnostics.

Preferably the binding sites are specific for a compound chosen from the group consisting of drugs, metabolites, nucleotides, nucleic acids, carbohydrates, proteins, hormones, toxins, steroids, prostaglandins and leukotrienes.

In one embodiment the binding sites are specific for theofylline or diazepam.

Suitable labels for use in the methods according to the invention are radioligands, enzymes, biotin, steroids, fluorochromes, gold.

The methods according to the invention are preferably used in immunoassays, especially in radioimmunoassays.

The method of therapy or diagnosis according to the invention comprises several different modes of action. For example, it can be used to withdraw an undesired organic molecule from a mammal body, such as a toxin. In another embodiment the artificial antibodies assemble around a cancer cell to indicate the presence of such a cell. In a further embodiment the artificial antibodies are bringing a drug to specific targets, for instance cancer cells.

In one embodiment of treating a mammal body an extra corporal device containing the artificial antibodies is coupled to the body via a shunt in the bloodstream, and the bloodstream is passed through the device.

For the studies the inventors chose two chemically unrelated drugs, theophylline and diazepam, as print molecules. Theophylline, a commonly used drug in the prevention and treatment of asthma, apnea and obstructive lung diseases, has a narrow therapeutic index (56–112 µmol $L^{-1}$ serum) requiring careful monitoring of serum concentrations[17]. Diazepam (e.g. valium) is a member of the benzodiazepine group of drugs widely used as hypnotics, tranquilizers and muscle relaxants[18]. Benzodiazepines are one of the most commonly implicated substances in drug overdose situations and their detection in body fluids is very useful in clinical and forensic toxicology. Current methods for measuring theophylline and benzodiazepines are based on high-performance liquid chromatography (HPLC)[19-21] and on immunological techniques[22-26].

Figure 2:
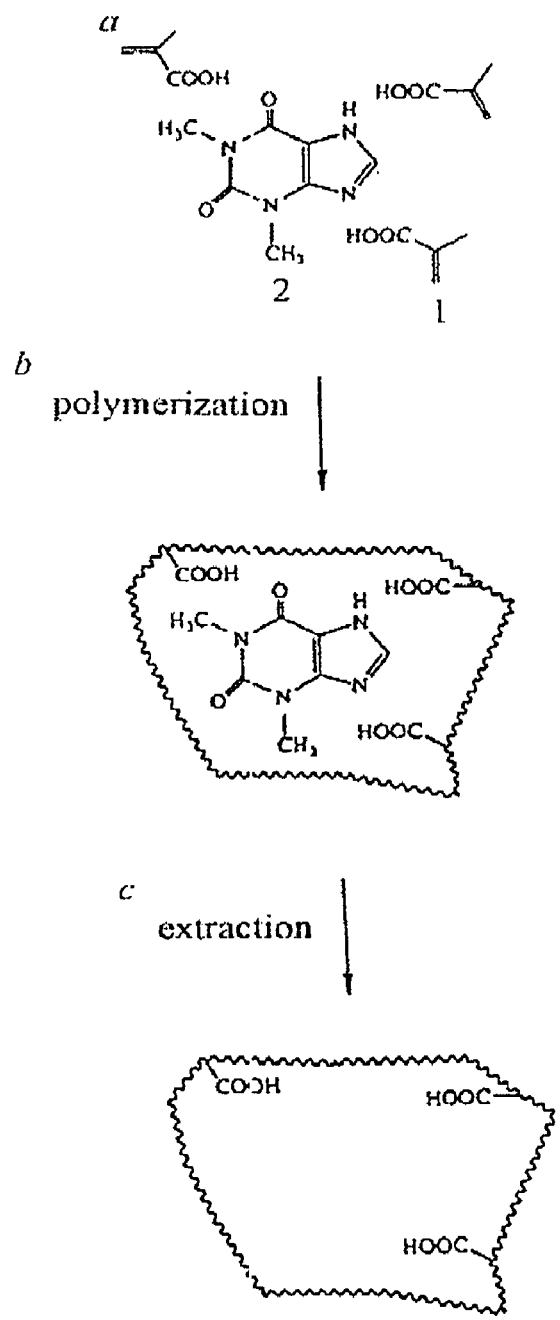
FIG. 2. Polymerisation of functional monomers in the presence of a print molecule.

The polymers were prepared using methacrylic acid (MAA) as the functional monomer and ethylene glycol dimethacrylate (EDMA) as the crosslinking monomer (FIG. 2). This is a well characterised polymer system that has been used for the preparation of molecular imprints against a number of compounds[12-14,16]. The carboxylic acid function of MAA has been shown to form ionic interactions with amino groups[12] and hydrogen bonds with polar functionalities of the print molecule[14]. The inventors assume that hydrogen bonding is the predominant type of force operating during imprinting and subsequent recognition in the present system. Dipole-dipole and hydrophobic interactions may also contribute.

The solvent compositions giving optimal binding and selectivity were determined for each polymer (see Example 2 and FIG. 1 below). As a general guide[14,27]: i) in a more apolar solvent the substrate binds more strongly to the polymer than in polar solvents, and ii) small amounts of acetic acid can be added to the solvent in order to supress non-specific binding. The equilibrium dissociation constants ($K_D$) for binding of the drugs to the corresponding polymers were estimated by Scatchard plot analysis using radio-labelled ligands. In both cases, the Scatchard plots were nonlinear and fitted well with two $K_D$ values, for high and low affinity binding sites. The inventors believe that, as in the case of polyclonal antibodies, the polymers contain a heterogenous population of sites with different affinities for the print molecule. The $K_D$ values for the high and low affinity binding sites, calculated with the LIGAND programme (Elsevier-Biosoft), were $3.46 \times 10^{-7}$ M and $6.55 \times 10^{-5}$ M (associated with a population of sites of 0.016 µmol g and 1.28 µmol $g^{-1}$, respectively) for theophylline and $3.76 \times 10^{-8}$ M and $7.36 \times 10^{-8}$ M (0.0071 µmol $g^{-1}$ and 0.51 µmol $g^{-1}$) for diazepam.

Polymers prepared against theophylline or diazepam were used as antibody-substitutes in the construction of competitive binding for theophylline and diazepam determination in human serum. The method, which we name Molecularly Imprinted Sorbent Assay (MIA), relies on the inhibition of binding of radio-labelled ligand by the serum analyte. The amount of radioligand bound to the polymer is inversely related to the concentration of drugs present in the sample. Drug free serum samples spiked with known amounts of theophylline or diazepam were used for establishing the standard calibration curves. Prior to the actual assay, the drug was extracted from the serum by standard protocols used for HPLC-analysis[19-21] (FIG. 1). The MIA for theophylline was linear over the range 14–224 µmol $L^{-1}$ which is satisfactory for therapeutic monitoring of the drug. The results for diazepam were linear over the range which is normally used in standard immunoassay techniques for benzodiazepines (0.44–28 µmol $L^{-1}$).

The specificity of the method was tested by the determination of cross-reactivity of major metabolites and of drugs structurally related to theophylline or diazepam (Table 1).

TABLE 1

Cross-reactivity of various xanthine and uric acid derivatives for binding of $^3$H-theophylline (bronchodilator) and various benzodiazepines for binding of $^3$H-diazepam (tranqilizer) to artificial antibodies (ArtAb's) and natural antibodies (Ab's).

| Theophylline antibodies | | | Diazepam antibodies | | |
|---|---|---|---|---|---|
| | Cross-reaction (%) | | | Cross-reaction (%) | |
| Competitive ligand | ArtAb | Ab* | Competitive ligand | ArtAb | Ab** |
| Theophylline (1,3-dimethyl-xantine) | 100 | 100 | Diazepam (e.g. valium) | 100 | 100 |
| 3-Methylxantin | 7 | 2 | Alprazolam | 40 | 44 |
| Xanthine | <1 | <1 | Demethyldiazepam | 27 | 32 |
| Hypoxanthine | <1 | <1 | | | |

TABLE 1-continued

Cross-reactivity of various xanthine and uric acid derivatives for binding of $^3$H-theophylline (bronchodilator) and various benzodiazepines for binding of $^3$H-diazepam (tranqilizer) to artificial antibodies (ArtAb's) and natural antibodies (Ab's).

| | Theophylline antibodies | | | Diazepam antibodies | |
|---|---|---|---|---|---|
| | Cross-reaction (%) | | Competitive | Cross-reaction (%) | |
| Competitive ligand | ArtAb | Ab* | ligand | ArtAb | Ab** |
| 7-(β-Hydroxyethyl)-1, 3-di-methylxanthine | <1 | <1 | Clonazepam | 9 | 5 |
| | | | Lorazepam | 4 | 1 |
| Caffeine (1,3,7-trimet-ylxanthine) | <1 | <1 | Chlordiaze-poxid | 2 | <1 |
| Theobromine (3,7-dimetylxanthine) | <1 | <1 | | | |
| Uric acid | <1 | <1 | | | |
| 1-Methyluric acid | <1 | <1 | | | |
| 1,3-Dimethyluric acid | <1 | <1 | | | |

The ligands were added to drug free serum and assayed as described in FIG. 1. Cross reactivities are expressed as the molar ratio of theophylline and diazepam, respectively, to ligand giving 50% inhibition of radioligand binding to polymer
*Data from ref 22.
**Data from ref 24.

The MIA method for theophylline (1,3-dimethylxanthine) appears to be highly specific since from all the compounds tested only 3-methylxanthine showed some cross-reactivity.

In the case of the diazepam assay several other benzodiazepines showed significant cross-reactivity. This was, however, expected because benzodiazepines are very similar in structure, as seen below:

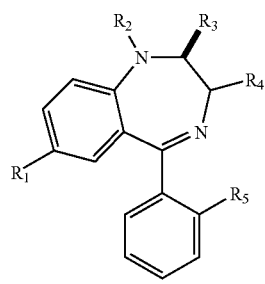

| | $R_1$ | $R_2$ | $R_3$ | $R_4$ | $R_5$ |
|---|---|---|---|---|---|
| Diazepam | Cl | Me | O | H | H |
| Desmethyldiazepam | Cl | H | O | H | H |
| Clonazepam | NO$_2$ | H | O | H | Cl |
| Lorazepam | Cl | H | O | OH | Cl |
| Alprazolam | Cl | | 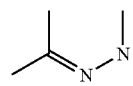 | H | H | and even antibodies have difficulty in distinguishing between them[25,26] (Table 1).

The ability of the MIA method for accurate measurement of theophylline was evaluated by analysing 32 patient serum samples. The sample were also analysed with the Enzyme-Multiplied Immunoassay Technique (EMIT)[28] and the comparison of the results obtained showed excellent correlation between the two methods (FIG. 1). Furthermore, the reliability of the assay was determined by measurement of theophylline samples of known concentration (three clinical significant concentrations; eleven repetitions; coefficient of variation $\leq 6.5\%$).

The results presented here demonstrate, for the first time, the ability to use chemically prepared macromolecules with preselected specificity, instead of the traditional biomolecules, as receptors in competitive binding assays. A great advantage of molecularly imprinted polymers is their simple and rapid (two to three days) preparation and their remarkable stability. They can be stored in the dry state, even at elevated temperatures, for several years without loss of recognition capabilities[27]. In addition, the potential to reuse the polymers may prove valuable. Furthermore, by analogy to immunoaffinity chromatography, molecularly imprinted polymers could be useful for the separation and isolation of different compounds. Apart from the practical importance of the described preparations, structural studies on the interactions of drugs with their artificial receptors could yield valuable insight into the nature of molecular recognition phenomena[29-31].

Molecular imprints may be obtained against functionality complementary to the monomer[14,27]. There is a potential for molecularly imprinted artificial antibodies in the analysis of many other drugs, metabolites, hormones, toxins, etc.

It is also noteworthy that molecularly imprinted polymers provide a potential alternative to the use of laboratory animals for the production of antibodies. Preliminary data from similar studies with an emphasis on recognition in aqueous systems using other compounds such as opiates and biologically active peptides, indicate that this technique promises to become widely useful.

The invention is described more in detail with reference to the following examples and the accompanying drawing.

FIG. 1 shows a comparison of the competitive binding assays Enzyme-Multiplied Immunoassay Technique (EMIT)[28] and MIA for determination of serum concentration av theophylline in patient samples (n=32).

EXAMPLE 1

Preparation of Molecularly Imprinted Polymers
The preparation follows the reaction of FIG. 2.

A) The functional monomer, methacrylic acid (MAA, 1), is mixed with the print molecule, here theophylline (2), and ethylene glycol dimethacrylate (EDMA), the crosslinking monomer, in a suitable solvent. MAA is selected for its ability to form hydrogen bonds with a variety of chemical functionalities of the print molecule.

B) The polymerisation reaction is started with the addition of initiator (AIBN) and a rigid insoluble polymer is formed. "Imprints", which are complementary in both shape and chemical functionality to the print molecule, are now present within the polymeric network.

C) The print molecule is removed by extraction.

The wavy lines in FIG. 2 represent an idealised polymer structure but do not take into account the accessibility of the substrate to the recognition site in the macroporous polymer structure.

Methods

Anti-Theophylline Polymer
To a glass bottle were added chloroform (250 ml), theophylline (4.7 g), MAA (9 g), EDMA (93.5 g) and 2,2'-azobis(2-methylpropionitrile) (AIBN, initiator, 1.2 g). The mixture was degassed under vacuum in a sonicating waterbath and sparged with nitrogen for 5 min. The polymerisation reaction took place at 60° C. for 24 h. The bulk polymer was grounded in a mechanical mortar and wet sieved (water) through a 25 μm sieve. The fines were removed by repeated settling in acetonitrile. The print molecule (theophylline) was extracted by extensive washing of the particles with methanol-acetic acid (9/1, v/v). Finally, the polymer particles were dried under vacuum and stored in a desiccator.

Anti-Diazepam Polymer

Diazepam (1.27 g) was mixed with MAA (2.26 g), EDMA (26.1 g) and AIBN (0.5 g) in chloroform (39 ml). The polymerisation mixture was degassed under vacuum in a sonicating water-bath, sparged with nitrogen and then polymerised under UV (366 nm) at 4° C. for 16 h. The resulting polymer was then treated as described above.

EXAMPLE 2

A comparison of the competitive binding assays Enzyme-Multiplied Immunoassay Technique (EMIT) 8 and MIA for determination of serum concentration of theophylline in patient samples (n=32) was performed. EMIT reagents were supplied by the manufacturer (SYVA, Palo Alto, USA). All enzyme immunoassays were preformed at the department of Clinical Pharmacology, University Hospital, Lund, Sweden, according to the method of the manufacturer. The result is shown in FIG. 1:

Slope: 0.99, Intercept: 1.50 μmol L$^{-1}$, correlation coefficient: 0.98.

Methods

The assay conditions were established by applying similar protocols as is standard for the optimisation of immunoassays using antibodies[32]. 40 μl of each sample was mixed with 40 μl of HCl (0.2 M) and extracted with 1 ml of dichloromethaneisopropanol (4/1, v/v). The organic layer was evaporated at 40° C. under a stream of nitrogen. The residue was redissolved in 100 μl of acetonitrile-acetic acid (99/1, v/v) containing [$^3$H]-theophylline (5 ng, 18.6 Ci mmol$^{-1}$). Polymer imprinted against theophylline was then added (12.5 mg of polymer in 0.9 ml of the same solvent) and the mixture was incubated for 15 h at room temperature. The binding equilibrium was reached after 8 h, 80 and 90% of the binding occurred within 3 and 5 h. After centrifugation, the unbound [3H]-theophylline in 200 μl of the supernatant was measured by liquid scintillation counting. The calibration graph was linear over the range 14–224 μmol L$^{-1}$ (correlation coefficient=0.999) and the detection limit of the assay was found to be 3.5 μmol L$^{-1}$. The diazepam assay, performed in a similar manner using 5 mg of polymer in toluene-heptane (4:1; v/v), was linear from 0.44 to 28 μmol L$^{-1}$ (correlation coefficient 0.991) with a detection limit of 0.2 μmol L$^{-1}$.

REFERENCES

1. Yalow, R. S. & Berson, S. A. Nature 184, 1648–1649 (1959).
2. Köhler, G. & Milstein, C. Nature 256, 495–497 (1975).
3. Oellerich, M. J. Clin. Chem. Clin. Biochem. 22, 895–904 (1984).
4. Gosling, J. P. Clin. Chem. 36, 1408–1427 (1990).
5. Kurstak, E. in Enzyme Immunodiagnosis (ed Kurstak, E.) 5–11 (Academic Press, London, 1986).
6. Ekberg, B. & Mosbach, K. Trends Biotechnol. 7, 92–96 (1989).
7. Wulff, G. Amer. Chem. Soc. Symp. Series 308, 186–230 (1986).
8. Shea, K. J. & Sasaki, D. Y. J. Am. Chem. Soc. 113, 4109–4120 (1991).
9. Robinson, D. K. and Mosbach, K. J. Chem. Soc. Chem. Commun. 14, 969–970 (1989).
10. U.S. Pat. No. 5,110,833 to Klaus Mosbach.
11. Sellergren, B., Ekberg, B. & Mosbach, K. J. Chromatogr. 347, 1–10 (1985).
12. Sellergren, B., Lepistö, M. & Mosbach, K. J. Am. Chem. Soc. 110, 5853–5860 (1988).
13. O'Shannessy, D. J., Ekberg, B., Andersson, L. I. & Mosbach, K. J. Chromatogr. 470, 391–399 (1989).
14. Andersson, L. I. & Mosbach, K. J. Chromatogr. 516, 313–322 (1990).
15. Wulff, G. & Minarik, M. J. Liq. Chromatogr. 13, 2987–3000 (1990).
16. Fischer, L., Müller, R., Ekberg, B. & Mosbach, K. J. Am. Chem. Soc. 113, 9358–9360 (1991).
17. Hendeles, L., Weinberger, M. & Johnson, G. Clin. Pharmacokinetics 3, 294–312 (1978).
18. Harvey, S. L. in The Pharmacological Basis of Therapeutics (eds Gilman, A. G., Goodman, L. S., Rail, T. W. & Murad, F.) 339–351 (Marcel Dekker Inc., New York, 1985).
19. Meffin, P. J. & Miners, J. O. in Progress in Drug Metabolism (eds Bridges, J. W. & Chasseaud, L. F.) Vol. 4, 261–307 (J. Wiley, London, 1980).
20. Peng, G. W., Gadalla, M. A. F. & Chiou, W. L. Clin. Chem. 24, 357–361 (1978).
21. Mura, P., Piriou, A., Fraillon, P., Papet, Y. & Reiss, D. J. Chromatogr. 416, 303–310 (1987).
22. Castro, A., Ibanez, J., Voight, W., Noto, T. & Malkus, H. Clin. Chem. 24, 944–946 (1978).
23. Chang, J., Gotcher, S. & Gushaw, J. B. Clin. Chem. 26, 361–367 (1982).
24. Ponceiet, S. M., Limet, J. N., Noel, J. P., Kayaert, M. C., Galanti, L. & Collet-Cassart, D. J. Immunoassay, 11, 77–88 (1990).
25. Baselt, R. C. in Advances in Analytical Toxicology (ed Baselt, R. C.) Vol. 1, 81–123 (Biomedical Publications, Foster City, Calif., 1984).
26. Aitunkaya, D. & Smith, R. N. Forensic. Sci. Int., 39, 23–37 (1988).
27. Andersson, L. I. thesis, Lund Univ. (1991).
28. Dietzler, D. N., Waldner, N., Tieber, V. L., McDonald, J. M., Smith, C. H., Ladenson, J. H. & Leckie, M. P. Clin. Chim. Acta 101, 163–181 (1980).
29. Cram, D. J. Nature 356, 29–36 (1992).
30. Rebek, J. Jr. Angew. Chem. Int. Ed. Engl. 29, 245–255 (1990).
31. Desiongchamps, G., Galán, A., de Mendoza, J. & Rebek, J. Jr. Angew. Chem. Int. Ed. Engl. 31, 61–63 (1992).
32. Tijssen, P. Laboratory Techniques in Biochemistry and Molecular Biology, Practice and Theory of Enzyme Immunoassays 5th printing (Elsevier Publishers B.V., Amsterdam, 1988).

The invention claimed is:

1. An artificial antibody comprising a crosslinked polymer prepared by molecular imprint polymerization and having a binding site having specificity for an imprinted molecule, wherein said artificial antibody has a particle size of less than about five microns.

2. The artificial antibody according to claim 1, wherein said particle size is between about 10 nm and 100 nm.

3. The artificial antibody according to claim 1, wherein said specific binding sites are specific for a drug molecule.

4. The artificial antibody according to claim 3, wherein said drug molecule is theophylline.

5. The artificial antibody according to claim 3, wherein said drug molecule is a benzodiazepine drug.

6. The artificial antibody according to claim 3, wherein said drug molecule is diazepam.

7. The artificial antibody according to claim 3, wherein said drug molecule has a narrow therapeutic index.

8. The artificial antibody according to claim 1, wherein said particle size is between about 10 nm and 1000 nm.

9. The artificial antibody according to claim 1, wherein said molecular imprint polymerization at least reacts a methacrylic acid molecule with an ethylene glycol dimethacrylate molecule.

10. The artificial antibody according to claim 1, wherein said molecular imprint polymerization reacts at least one molecule of itaconic acid, vinylpyridine, vinylimidazole, or alkylated hydrophobic monomer.

11. The artificial antibody according to claim 1, wherein said binding site is specific for at least a nucleic acid or a nucleotide.

12. The artificial antibody according to claim 1, wherein said binding site is specific for a metabolite.

13. The artificial antibody according to claim 1, wherein said binding site is specific for a toxin.

14. The artificial antibody according to claim 1, wherein said binding site is specific for a prostaglandin molecule.

15. The artificial antibody according to claim 1, wherein said binding site is specific for a hormone.

16. The artificial antibody according to claim 1, wherein said binding site is specific for an opiate molecule.

17. A method for determining the amount of an organic molecule in a fluid, comprising the steps of:
obtaining a fluid sample having an organic molecule,
adding a known amount of a labeled organic molecule to said sample,
contacting said sample with an artificial antibody comprising a crosslinked polymer prepared by molecular imprint polymerization and having a binding site having specificity for said organic molecule, wherein said artificial antibody has a particle size of less than about five microns,
binding said organic molecule with said artificial antibody so that said organic molecule and said labeled organic molecule in said sample competitively bind with said artificial antibody; and determining the amount of said labeled organic molecule unbound in said sample or bound to said artificial antibody so as to determine the amount of said organic molecule in said fluid.

18. The method according to claim 17, wherein said label comprises at least a radioligand, an enzyme, biotin, a steroid, or a fluorochrome.

19. The method according to claim 17, wherein a label of said labeled organic molecule is gold.

20. The method according to claim 17, wherein a label of said labeled organic molecule comprises at least an electrochemiluminescent compound.

21. The method according to claim 17, in which said particle size is between about 10 nm and 100 nm.

22. The method according to claim 17, in which said particle size is between about 10 nm and 1000 nm.

23. The method according to claim 21, in which a label of said labeled organic molecule comprises at least an electrochemiluminescent compound.

24. The method according to claim 22, in which a label of said labeled organic molecule comprises at least an electrochemiluminescent compound.

25. A method of therapy, comprising:
providing an artificial antibody comprising a crosslinked polymer prepared by molecular imprint polymerization for a target and having a binding site with specificity for said target, wherein said artificial antibody has a particle size less than about five microns, and
treating a patient having a bodily fluid having said target by providing said artificial antibody to said bodily fluid and specifically binding the target and said artificial antibody forming a bound target,
withdrawing said bound target from said bodily fluid of said mammal body having said target.

26. A method of therapy according to claim 25, further comprising the step of:
administering said artificial antibody to the body of a patient.

27. A method of therapy according to claim 25, further comprising the steps of:
removing said bodily fluid having said target from a patient,
conducting said specifically binding in an extra-corporal device containing said artificial antibody.

28. A method of therapy according to claim 27, further comprising the step of:
returning said bodily fluid to said patient after said withdrawing said bound target.

29. The method according to any one of claims 25–28, in which said target imprinted molecule is a toxin.

30. The method according to any one of claims 25–28, in which said target is a cancer cell comprises said imprinted molecule.

31. The method according to claim 17, in which said organic molecule is drug molecule.

32. The method according to claim 17, in which said organic molecule is a metabolite.

33. The method according to claim 17, in which said organic molecule is a nucleotide.

34. The method according to claim 17, in which said organic molecule is a nucleic acid.

35. The method according to claim 17, in which said organic molecule is a carbohydrate.

36. The method according to any one of claims 17, 21 and 22, in which said organic molecule is a protein.

37. The method according to any one of claims 17, 21 and 22, in which said organic molecule is a hormone.

38. The method according any one of claims 17, 21 and 22, in which said organic molecule is a toxin.

39. The method according to claim 17, in which said organic molecule is a prostaglandin.

40. The method according to claim 17, in which said organic molecule is a leukotriene.

41. The method of therapy according to claim 25, further comprising the steps of:
removing said bodily fluid having said artificial antibody from said patient, and
returning said bodily fluid to said patient after said withdrawing step.

* * * * *